(12) United States Patent
Krukonis et al.

(10) Patent No.: US 7,186,796 B2
(45) Date of Patent: Mar. 6, 2007

(54) METHOD FOR DRYING WATER-BORNE MATERIALS

(75) Inventors: Val Krukonis, Lexington, MA (US); Kara T. Williams, Saugus, MA (US); Anthony Gudinas, Atkinson, NH (US); Hans Schonemann, Newburyport, MA (US); Paula Wetmore, Chelmsford, MA (US)

(73) Assignee: Phasex Corporation, Lawrence, MA (US)

( * ) Notice: Subject to any disclaimer, the term of this patent is extended or adjusted under 35 U.S.C. 154(b) by 331 days.

(21) Appl. No.: 10/373,542

(22) Filed: Feb. 25, 2003

(65) Prior Publication Data

US 2004/0014084 A1    Jan. 22, 2004

Related U.S. Application Data

(60) Provisional application No. 60/359,665, filed on Feb. 25, 2002.

(51) Int. Cl.
*A61K 38/28* (2006.01)
*A61K 9/14* (2006.01)
*A61K 9/127* (2006.01)
*G01N 33/00* (2006.01)

(52) U.S. Cl. .................. 530/303; 430/350; 430/399; 424/45; 424/46; 424/450; 424/491; 424/499; 422/68.1; 422/81; 422/101

(58) Field of Classification Search ............... 530/303, 530/350, 399, 412; 424/45, 46, 450, 491, 424/499; 422/68.1, 81, 101
See application file for complete search history.

(56) References Cited

U.S. PATENT DOCUMENTS

| 4,069,351 | A |   | 1/1978 | Yano et al. |         |
|-----------|---|---|--------|-------------|---------|
| 4,157,404 | A |   | 6/1979 | Yano et al. |         |
| 5,707,634 | A |   | 1/1998 | Schmitt     |         |
| 5,776,486 | A | * | 7/1998 | Castor et al. | 424/450 |
| 6,051,694 | A | * | 4/2000 | Castor et al. | 530/418 |

FOREIGN PATENT DOCUMENTS

| GB | 1 347 727    | 2/1974  |
| WO | WO 97/14407  | 4/1997  |
| WO | WO 98/16204  | 4/1998  |
| WO | WO 99/65469  | 12/1999 |
| WO | WO 00/30612  | 6/2000  |

OTHER PUBLICATIONS

International Search Report from PCT/US03/05592 (mailing date Aug. 7, 2003).
Hock S Tan & Suresh Borsadia, Particle Formation Using Supercritical Fluids: Pharmaceutical Applications, Exp. Opin. Ther. Patents, 2001, pp. 861-872, 11(5).
Jennifer Jung & Michel Perrut, Particle Design Using Supercritical Fluids: Literature and Patent Survey, Journal of Supercritical Fluids, 2001, pp. 179-219, 20.

* cited by examiner

*Primary Examiner*—Jon Weber
*Assistant Examiner*—Abdel A. Mohamed
(74) *Attorney, Agent, or Firm*—Lucas & Mercanti, LLP

(57) ABSTRACT

Provided is a method of isolating a bio-molecule from a water-borne mixture, the method comprising: contacting the water-borne mixture with dimethyl ether to form solid particles of the bio-molecule.

**

METHOD FOR DRYING WATER-BORNE MATERIALS

This application claims priority from U.S. Provisional Application Ser. No. 60/359,665, filed Feb. 25, 2002, he disclosure of which is hereby incorporated by reference as if fully set forth herein.

The present invention relates to a method for isolating dried solid particles from a water-borne mixture.

The recovery of a material dissolved or suspended in water is a common need in industry, and removal of water by drying is common. For example, large quantities of food and milk are dried to facilitate long term storage. Sterilized solutions or water suspensions of pharmaceuticals are dried for subsequent ease in preparing exact dosage forms. Many chemicals including dyes and pigments are synthesized in aqueous solutions or suspensions, and are subsequently isolated by drying. Typical drying methods include spray drying, belt drying, freeze drying (also known as lyophilization) and critical point drying. The selection of the drying method in each case is dependent upon the desired properties in the dried material such as stability, pharmaceutical activity, or particle size.

While useful in many applications, known drying methods are often unsatisfactory for drying water-borne mixtures containing bio-molecules (e.g., peptides, proteins, DNA, RNA, and polysaccharides). For example, human blood typically cannot be isolated by spray drying techniques due to insufficient heat stability of some of the proteins contained therein. Similarly, pharmaceutical proteins (e.g., growth factors, vaccines, hormones, monoclonal antibodies and many therapeutic proteins) cannot generally be spray-dried due to their tendency to denature under the process conditions. Moreover, ultra-fine or microporous materials from water-borne mixtures cannot generally be isolated by spray-drying, belt drying or tray drying if retention of ultra-fine size or porosity is desired in the isolated material. These drying techniques often result in strong physical aggregation and severe pore collapse of the particles due to the large surface tension forces active during the vaporization of water.

Techniques that include the use of supercritical or near critical fluids have been utilized in alternative drying techniques. These techniques generally include the use of carbon dioxide or other fluids that are immiscible in water, and they also generally use an organic solvent, typically ethanol. Contact of the bio-molecule with such organic solvent-fluid-water mixtures often results in irreversible degradation of fragile bio-molecules. This process can also cause unfolding or denaturation of proteins which can result in loss of the proteins' bioactivity.

To avoid these difficulties, critical point drying can be used to form particles that maintain the shape and structure of the substrate. Critical point drying processes include the steps of soaking a water-borne mixture with a water-miscible organic solvent, e.g., acetone, ethanol; introducing carbon dioxide to the mixture to form a carbon-dioxide-solvent solution; raising the temperature of the system to above the critical point temperature of the carbon-dioxide-solvent solution; and removing the now gaseous solution while maintaining the temperature above the critical point temperature of the carbon dioxide-solvent solution to isolate the dried particles. While critical point drying achieves the formation of solid particles without pore collapse or strong physical aggregation of the particles, the entire process is a laborious one. In certain cases the technique can also result in the denaturation of the bio-molecules and a drastic decrease in the bio-molecules' bioactivity.

SUMMARY OF THE INVENTION

In one embodiment, the invention relates to a method of isolating a bio-molecule from a water-borne mixture. The method includes the step of contacting the water-borne mixture with dimethyl ether to form solid particles of the bio-molecule. Water-borne mixtures include aqueous solutions, suspensions, emulsions, micro-emulsions and liposomes suspended in aqueous media. The water-borne mixture includes the bio-molecule and a solvent component.

In one embodiment, the method is conducted at a temperature of 0 to 250° C., and the dimethyl ether is at a pressure range from $P_c$ to $10\times P_c$, wherein $P_c$ is the critical pressure of dimethyl ether. Preferably, the method is conducted at a temperature of 0 to 80° C., and the dimethyl ether is at a pressure range from $P_c$ to $2\times P_c$.

In another embodiment, the method is conducted at a temperature of 0 to 126.5° C. and the dimethyl ether is at a pressure range from 100 psi to $2\times P_c$. Preferably, the method is conducted at a temperature of 0 to 60° C., and the dimethyl ether is at a pressure range from 200 psi to $P_c$.

In still another embodiment, the method is conducted is conducted at a temperature of 0 to 126.5° C. and the dimethyl ether is at a pressure range from 50 psi to $P_c$. Preferably, the method is conducted at a temperature of 0 to 60° C.

In one aspect of the method (the static method), the bio-molecule is isolated from the water-borne mixture by introducing the dimethyl ether into a pressurized chamber containing the water-borne mixture. In another aspect of the method (the dynamic method), the bio-molecule is isolated by injecting the water-borne mixture into a stream of the dimethyl ether.

In one preferred embodiment, the isolated bio-molecule is a protein. For example, the method of the invention can be used to isolate a hormone such as insulin. The method of the invention is also useful for isolating an enzyme (e.g., chymotrypsin) from a water-borne mixture which can be recovered with minimal, if any, loss of catalytic activity.

In another preferred embodiment, the isolated bio-molecule is a polynucleotide such as DNA.

BRIEF DESCRIPTION OF THE DRAWINGS

FIG. 1 is a depiction of one embodiment of an apparatus useful for conducting the invention method.

FIG. 2 is a depiction of another embodiment of an apparatus useful for conducting the invention method.

DEFINITIONS

The definitions of certain terms used herein are as follows: "bio-molecule" refers to peptides, proteins, polynucleotides and polysaccharides. "water-borne mixture" refers to aqueous solutions, suspensions, emulsions, microemulsions and liposomes suspended in aqueous media.

DETAILED DESCRIPTION OF THE INVENTION

In accordance with the invention, Applicants have found a method for isolating a substance from a water-borne mixture containing the substance by contacting the water-borne mixture with compressed dimethyl ether to form solid particles of the substance. The invention provides a robust, scaleable, low-cost process for separating water from solid particles while maintaining the product's desired characteristics. The method achieves the drying of particles without significant particle aggregation from water-borne mixtures, including solutions and suspensions. The combination of these product characteristics and the compatibility with water-soluble or water-dispersible substances makes the process of the invention particularly desirable for biomolecules such as polypeptides, proteins, polynucleotides and polysaccharides.

Applicants have found that compressed gaseous, liquid or supercritical dimethyl ether is particularly advantageous for drying particles from water-borne mixtures using extraction techniques. Dimethyl ether (also known as methyl ether) is very soluble in water, and also dissolves water. This solubility is maintained along the entire vapor-pressure curve of dimethyl ether from about −5° C. to above its critical temperature (Tc) of 126.9° C. While not being bound by theory, Applicants believe the drying of porous particles without pore collapse is achieved because dimethyl ether and water form a single phase during the extraction process. The formation of a single phase is beneficial in overcoming the difficulties that typically plague processes that entail vaporization of water from a two-phase system of liquid water and water vapor. Other commonly used fluid solvents such as carbon dioxide, nitrous oxide, hydrocarbons and xenon are insoluble in water, and therefore do not achieve a single phase with water.

In one embodiment of the method, particles of desired substance are dried by charging a water-borne mixture into a drying chamber and then introducing gaseous dimethyl ether into the chamber. This static method can be considered as a water-extraction method as the aqueous solvent is extracted by the dimethyl ether leaving the dried particles in the drying chamber.

Figure 2:
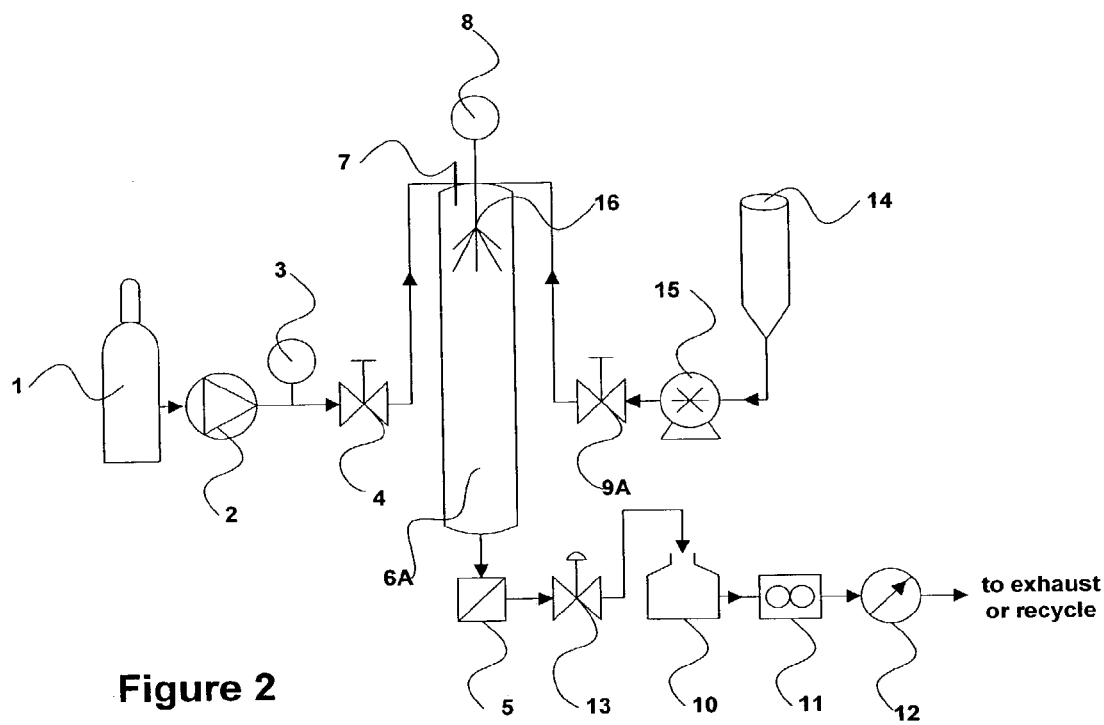
Figure 1:
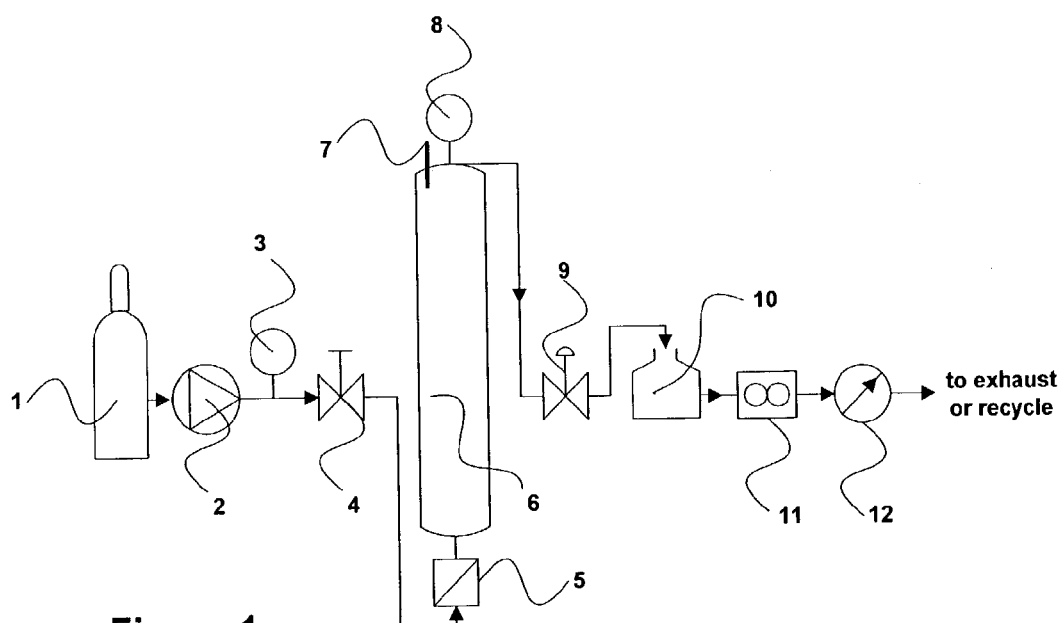

FIG. 1 shows one embodiment of an apparatus that can be used for conducting the static water-extraction method described above. The apparatus depicted in FIG. 1 includes a gas source housed in a pressurized cylinder 1, a gas compressor 2, and a pressure resistant drying chamber 6. The water-borne mixture containing the desired substance is charged to the drying chamber 6. The dimethyl ether (gas or liquid) is taken from the pressure cylinder 1 and compressed by gas pump 2. At a set pressure, monitored by pressure gauge 3, the dimethyl ether is fed through a needle valve 4 and introduced into the drying chamber 6. The dimethyl ether extracts the aqueous solvent component leaving dried solid particles in the filter 5, located within the pressurized drying chamber itself or positioned directly at the inlet of the chamber. A pressure reduction valve 9, located at the outlet of the chamber controls the dimethyl ether flow rate. A liquid collector 10, traps the water and liquid solvent, while a thermocouple 7, and a pressure gauge 8, monitors the conditions inside the chamber 6. A flow meter 11 and dry test meter 12, positioned downstream of the liquid collector 10, measure dimethyl ether flow rate and total volume, respectively. Dimethyl ether can be recycled using a closed loop to avoid dimethyl ether emission to the environment.

According to this static method, the size and morphology of the particles produced from a solution are often determined in large part by the properties of the solute substance itself, but certain process parameters can also often be manipulated to achieve the desired morphology and size of the dried particles. These parameters are apparent to those of ordinary skill in the art and include solute concentration, contact time in the drying chamber, temperature, pressure and nozzle size.

In another embodiment of the method, the water-borne mixture containing the desired substance, either in solution or suspension, is sprayed through an atomization nozzle into an established stream of dimethyl ether in a pressurized drying chamber. In the case of this dynamic method, the dimethyl ether extracts the aqueous solvent component causing the desired substance to precipitate as dried solid particles.

FIG. 2 shows an apparatus for conducting the dynamic method described above. In the apparatus, dimethyl ether, gas or liquid, is stored in pressurized cylinder 1. The fluid solvent exits cylinder 1 and is compressed by gas pump 2. At a predetermined pressure, monitored by pressure gauges 3 and 8, the fluid solvent traverses needle valve 4 and enters a pressure resistant drying chamber 6A. Once a desired supercritical solvent flow is established by adjusting valve 4, which is monitored by flow meter 11, a water-borne mixture containing the desired substance is fed from the solution reservoir 14 to the liquid gas pump 15 via needle valve 9A. The water-borne mixture subsequently enters the gas stream via a nozzle 16, which is disposed within the drying chamber 6A. The interaction between the supercritical fluid and aqueous solution, through nozzle 16, facilitates nucleation. A filter 5 traps the solid, stable particles that are recrystallized or dried, and liquid collector 10, traps the aqueous medium. A back pressure regulator 13, disposed downstream of drying chamber 6A, regulates the pressure inside the chamber. A thermocouple 7 and pressure gauge 8 monitor the conditions inside chamber 6A. A flow meter 11 and dry test meter 12, disposed downstream of back pressure regulator 13 measure the supercritical fluid's flow rate and total volume, respectively.

In this dynamic method, the rates of dimethyl ether addition to the water-borne mixture addition can be altered to achieve the desired particle size and shape. Other parameters, apparent to those of ordinary skill in the art, can also be manipulated such as contact time in the drying chamber, temperature, pressure and nozzle size.

The water-borne mixture includes the desired substance and a solvent component, that is composed in large part by water. Generally, the solvent component contains a significant proportion of water; typically at least 20%, preferably at least 40% by volume water, and more preferably at least 80% by volume water. In addition to water, the solvent component can also include other water-miscible solvents in mixture with water including but not limited to lower alcohols (e.g., methanol, ethanol, n-propanol, isopropanol), lower ketones (e.g., acetone) acetonitrile, methyl sulfoxide, dimethylformamide, ethers (e.g., diethyl ether), lower esters (e.g., ethyl acetate) and mixtures thereof.

The dried product from the process can be used for long-term storage of edible and potable foodstuffs, for pharmaceutical purposes for both human and veterinary applications (therapeutic, prophylactic and diagnostic purposes), for cosmetic applications or in other applications where a water-soluble or water-dispersible substrate is to be comminuted. In instances where the substances are used for pharmaceutical purposes, the dried substance can be administered alone or it can be further processed in combination with known excipients in conventional pharmaceutical formulations. These pharmaceutical agents or formulation thereof can be administered by oral, nasal, rectal, buccal, intraocular, pulmonary, transdermal, or parenteral routes.

In a preferred embodiment of the invention, the substance to be dried includes a bio-molecule selected from the group consisting of peptides, proteins, polynucleotides (e.g., DNA, RNA) and polysaccharides (e.g., heparin). For instance, the methods of the invention are useful for drying milk which is an aqueous emulsion containing proteins as well as lipids. The methods of the invention are particularly useful for drying protein particles, as the effects of the drying process on the tertiary structures of the proteins are minimal. As a result, the biological activity in the dried protein particles are maintained. Similarly, the structural integrity of the polynucleotides are also maintained by the drying methods of the invention. In one preferred embodiment, the bio-molecules are non-acid labile substances.

The method can be conducted at operating temperatures of about 0° C. to 250° C., preferably at 0° C. to 60° C. The pressure of the drying column is preferably maintained at about 50 to about 3,000 psi, more preferably about 100 to about 700 psi.

In one preferred embodiment of the method, the dimethyl ether is at a pressure equal to $P_c$ to $10\times P_c$, wherein $P_c$ is the critical pressure of dimethyl ether (53.7 bar). More preferably, the dimethyl ether is at a pressure equal to of $P_c$ to $2\times P_c$. In this embodiment, the method is preferably conducted at a temperature of 0 to 250° C., more preferably at a temperature of 0 to 80° C.

In another preferred embodiment of the method, the dimethyl ether is at a pressure of 100 psi to $2\times P_c$. More preferably, the dimethyl ether is at a pressure of 200 psi to $P_c$. In this embodiment, the method is preferably conducted at a temperature of 0 to 126.5° C., more preferably at a temperature of 0 to 60° C.

In another preferred embodiment of the method, the dimethyl ether is at a pressure of 50 psi to $P_c$. In this embodiment, the method is preferably conducted at a temperature of 0 to 126.5° C., more preferably at a temperature of 0 to 60° C.

The invention also provides a method for removing impurities from a desired substance. The impurities are extracted from the desired substance by the compressed dimethyl ether during the process of drying as described above, either according to the static or the dynamic method.

The invention also provides a method of removing infectious agents from a desired substance, as compressed dimethyl ether is an effective biocide against bacteria, fungi and viruses.

The following examples further illustrate the present invention, but of course, should not be construed as in any way limiting its scope.

EXAMPLE 1

Preparation of Dried Skim Milk

Skim milk, which contains both soluble and suspended protein was loaded into the solution reservoir. The dimethyl ether was introduced into the pressurized drying vessel at 25° C. and 1000 psi. A gas flow rate of 145 g/min of dimethyl ether was established. The milk was introduced into the dimethyl ether stream in the pressurized vessel at a volumetric flow rate of 3–6 mL/min. with an orifice of 50 μm. Dried, stable, free flowing particles of 1–2 μm were collected on the filter.

EXAMPLE 2

Preparation of Dried Silica

A 20 wt. % suspension of 200 nm size silica gel in water was charged to a pressure drying vessel and the vessel was sealed. Dimethyl ether was supplied to the drying chamber at 130° C. and 1500 psi. Dimethyl ether extracted the suspension at a ratio of 5 g of dimethyl ether/1 g of suspension. The silica was recovered as a free flowing powder consisting of 175–375 nm spheres.

EXAMPLE 3

Preparation of Dried Chymotrypsin

Fragments of chymotrypsin (20 to 80 μm in diameter) were dissolved in water to produce a 0.5% by weight aqueous solution. The solution was then charged into the solution reservoir. The dimethyl ether was introduced into the pressurized drying/particle formation vessel at 24° C. and 2500 psi. When the gas flow rate of about 100 SLPM (standard liter per minute) was established, the chymotrypsin solution was pumped into the system at a volumetric flow rate of 1.6 mL/min. The protein solution was atomized into the dimethyl ether gas stream via a 63 μm nozzle. The dissolved protein was precipitated from the solution and dried by dissolution of the water in the dimethyl ether. Dry, stable free-flowing protein powder was collected in the filter. Scanning electron microscopy revealed the processed protein particles were mostly spherical and in the range of 0.4 to 0.8 μm in diameter. Chymotrypsin was analyzed for activity according to the standard method specified in The United States Pharmacopeia/The National Formulary (USP 25/NF 20), $25^{th}$ Edition, pages 416–417. Analysis indicated that 95% of activity was maintained. Moisture analysis indicated that the residual moisture of the processed powder was 7.4%, which was the same as that of the unprocessed raw (starting) material.

EXAMPLE 4

Preparation of Dried Bovine Serum Albumin

A bovine serum albumin (BSA) aqueous solution containing 2.0% by weight of albumin was prepared and charged into the solution reservoir. The dimethyl ether was introduced into the pressurized drying/particle formation vessel at 40° C. and 2300 psi. When the gas flow rate of about 100 SLPM was established, the BSA solution was pumped into the system at a volumetric flow rate of 1.6 mL/min. The protein solution was atomized into the dimethyl ether gas stream via a 63 μm nozzle. The dissolved protein was precipitated from the solution and dried by dissolution of the water in the dimethyl ether. Dry, stable free-flowing protein powder was collected in the filter. Scanning electron microscopy revealed the processed protein particles were spherical and in the submicron range. Fourier transform infrared (FTIR) analysis was used to characterize the protein structure. Particle size measurement using laser diffraction technique shows that the processed particles had a median diameter of 2.8 μm. The secondary structure of BSA was quantified by Gaussian curve-fitting of the resolution-enhanced amide I band using a Magna-IR system (Nicolet, Wis., USA). This analysis indicated that the structural activity of the protein was maintained. Moisture analysis indicates that the residual moisture of the processed powder was 7.2%, which was about the same as that of the unprocessed raw (starting) material.

EXAMPLE 5

Preparation of Dried Bovine Insulin

A bovine insulin (zinc) aqueous solution containing 1.5% by weight of insulin was prepared in 0.01 M hydrochloride (HCl) solution and charged into the solution reservoir. Dimethyl ether was introduced into the pressurized drying/particle formation vessel at 37° C. and 2300 psi. When the gas flow rate of about 100 SLPM was established, the insulin solution was pumped into the system at a volumetric flow rate of 1.6 mL/min. The protein solution was pulverized into the dimethyl ether gas stream via a 63 μm nozzle. The dissolved protein was precipitated from the solution and dried by dissolution of the water in the dimethyl ether. Dry, stable free-flowing protein powder was collected in the filter. Scanning electron microscopy revealed the processed protein particles were mostly spherical and in the 1–4 μm range. Particle size measurement using laser diffraction technique shows that the processed particles have a median diameter of 2.8 μm. Analysis indicated that 100% of activity was maintained. Moisture analysis indicated that the residual moisture of the processed powder was 8.4%, which was about the same as that of the dry unprocessed raw (starting) material.

EXAMPLE 6

Preparation of Dried DNA

Unprocessed DNA material, composed of chunky strands, was dissolved in water to form an aqueous solution of DNA containing 0.5% by weight of DNA. The solution was charged into the solution reservoir. The dimethyl ether was introduced into the pressurized drying/particle formation vessel at 37° C. and 2500 psi. When a gas flow rate of about 100 SLPM was established, the DNA solution was pumped into the system at a volumetric flow rate of 1.6 mL/min. The DNA solution was atomized into the dimethyl ether gas stream via a 63 μm nozzle. The dissolved DNA was precipitated from the solution and dried by dissolution of the water in dimethyl ether. Dry, stable free-flowing powder was collected in the filter. Scanning electron microscopy revealed the processed protein particles were spherical and in the range of 0.5 to 1.0 μm in diameter.

What is claimed:

1. A method of isolating a bio-molecule from a water-borne mixture, the method comprising: removing an aqueous solvent from the water-borne mixture by contacting the water-borne mixture with dimethyl ether to form solid particles of the bio-molecule.

2. The method as recited in claim 1, wherein the water-borne mixture comprises the bio-molecule and a solvent component.

3. The method as recited in claim 1, wherein the water-borne mixture is a suspension.

4. The method as recited in claim 1, wherein the contacting is conducted at a temperature of 0 to 250° C. and the dimethyl ether is at a pressure range from $P_c$ to $10\times P_c$, wherein $P_c$ is the critical pressure of dimethyl ether.

5. The method of claim 4, wherein the contacting is conducted at a temperature of 0 to 80° C. and the dimethyl ether is at a pressure range from $P_c$ to $2\times P_c$.

6. The method as recited in claim 1, wherein the contacting is conducted at a temperature of 0 to 126.5° C. and the dimethyl ether is at a pressure range from 100 psi to $2\times P_c$, wherein $P_c$ is the critical pressure of dimethyl ether.

7. The method as recited in claim 6 wherein the contacting is conducted at a temperature of 0 to 60° C. and the dimethyl ether is at a pressure range from 200 psi to $P_c$.

8. The method as recited in claim 1, wherein the contacting is conducted at a temperature of 0 to 126.5° C. and the dimethyl ether is at a pressure range from 50 psi to $P_c$, wherein $P_c$ is the critical pressure of dimethyl ether.

9. The method as recited in claim 8 wherein the contacting is conducted at a temperature of 0 to 60° C.

10. The method as recited in claim 1, wherein the dimethyl ether is introduced into a pressurized chamber containing the water-borne mixture.

11. The method as recited in claim 1, wherein the water-borne mixture is injected into a stream of the dimethyl ether.

12. The method as recited in claim 1, wherein the bio-molecule is a protein.

13. The method as recited in claim 12, wherein the protein is a hormone.

14. The method as recited in claim 13, wherein the hormone is insulin.

15. The method as recited in claim 12, wherein the protein is an enzyme.

16. The method as recited in claim 1, wherein the bio-molecule is a polynucleotide.

17. The method as recited in claim 16, wherein the polynucleotide is DNA.

18. A method of isolating a material from a water borne mixture, the method comprising: removing an aqueous solvent from the water-borne mixture by contacting the water borne mixture with dimethyl ether to form dry particle of the material.

19. The method as recited in claim 18, wherein the material is an organic substance.

20. The method as recited in claim 18, wherein the material is an inorganic substance.

21. The method as recited in clam 18, wherein the material in an edible or potable foodstuff.

22. The method as recited in claim 18, wherein the water-borne mixture comprises the material and a solvent component.

23. The method as recited in claim 18, wherein the material is silica gel.

24. The method as recited in claim 18, wherein the material is a pharmaceutical.

25. The method as recited in claim 18, wherein the water-borne mixture is a suspension.

26. The method as recited in claim 18, wherein the water-borne mixture is an emulsion.

27. The method as recited in claim 18, wherein the water-borne mixture is a micro-emulsion.

28. The method as recited in claim 18, wherein the water-borne mixture comprises liposome suspended in aqueous media.

29. The method as recited in claim 18, wherein the water-borne mixture is an aqueous solution.

30. The method as recited in claim 18, wherein the contact is conducted at a temperature of 0 to 250° C. and the dimethyl ether is at a pressure range of 50 psi to $10\times P_c$, wherein $P_c$ is the critical pressure of dimethyl ether.

31. The method as recited in claim 18, wherein the contact is conducted at a temperature of 0 to 126.5° C. and the dimethyl ether is at a pressure range of 50 psi to $2\times P_c$, wherein $P_c$ is the critical pressure of dimethyl ether.

32. The method as recited in claim 18, wherein the dimethyl ether is introduced into a pressurized chamber containing the water-borne mixture.

33. The method as recited in claim 18, wherein the water-borne mixture is injected into a stream of dimethyl ether.

34. A method of purifying a desired substance contaminated with impurities contained in a water-borne mixture, the method comprising contacting the water-borne mixture with dimethyl ether to remove an aqueous solvent and the impurities from the desired substance.

* * * * *